(12) United States Patent
Okihara

(10) Patent No.: US 11,311,680 B2
(45) Date of Patent: Apr. 26, 2022

(54) FEMALE SYRINGE AND SYRINGE KIT

(71) Applicant: TERUMO KABUSHIKI KAISHA, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 145 days.

(21) Appl. No.: 16/577,501

(22) Filed: Sep. 20, 2019

(65) Prior Publication Data
US 2020/0009326 A1    Jan. 9, 2020

Related U.S. Application Data

(63) Continuation of application No. PCT/JP2018/010267, filed on Mar. 15, 2018.

(30) Foreign Application Priority Data

Mar. 22, 2017    (JP) .............................. JP2017-055227

(51) Int. Cl.
*A61M 5/315* (2006.01)
*A61M 5/178* (2006.01)
(Continued)

(52) U.S. Cl.
CPC ...... *A61M 5/31596* (2013.01); *A61M 5/1782* (2013.01); *A61M 5/19* (2013.01);
(Continued)

(58) Field of Classification Search
CPC .. A61M 5/31596; A61M 5/1782; A61M 5/19; A61M 5/3129; A61M 2005/3131;
(Continued)

(56) References Cited

U.S. PATENT DOCUMENTS 3,511,239 A * 5/1970 Tuschhoff ............. A61M 5/284
    604/89
4,781,701 A * 11/1988 Geprags ................ A61M 5/344
    604/240

(Continued)

FOREIGN PATENT DOCUMENTS

EP    0 956 849 A2    11/1999
EP     0956849    *    11/1999
(Continued)

OTHER PUBLICATIONS

International Searching Authority, "International Search Report" and "Written Opinion" issued in connection with International Patent Application No. PCT/JP2018/010267, dated Apr. 17, 2018.
(Continued)

*Primary Examiner* — Theodore J Stigell
(74) *Attorney, Agent, or Firm* — Foley & Lardner LLP

(57) ABSTRACT

A female syringe of a syringe kit includes a female syringe barrel including a cylindrical portion into which a nozzle of a male syringe is insertable, a hollow cylindrical packing arranged in the cylindrical portion, and a cap detachably attached to the cylindrical portion. When the cap is detached from the cylindrical portion, the packing remains in the cylindrical portion, a distal end opening is opened, and the nozzle of the male syringe is fitted in a liquid-tight manner to an inner side of the packing.

14 Claims, 9 Drawing Sheets

(51) Int. Cl.
*A61M 5/19* (2006.01)
*A61M 5/31* (2006.01)

(52) U.S. Cl.
CPC ... *A61M 5/3129* (2013.01); *A61M 2005/3131* (2013.01); *A61M 2005/31598* (2013.01)

(58) Field of Classification Search
CPC .......... A61M 2005/31598; A61M 2005/3103; A61M 2039/0027; A61M 2039/1083; A61M 5/2066; A61M 5/3134
See application file for complete search history.

(56) References Cited

U.S. PATENT DOCUMENTS

| | | | | |
|---|---|---|---|---|
| 5,135,496 | A | * | 8/1992 | Vetter ...................... A61M 5/34 604/111 |
| 5,624,405 | A | * | 4/1997 | Futagawa ................ A61M 5/28 604/199 |
| 7,041,087 | B2 | * | 5/2006 | Henderson ............ A61M 5/345 604/200 |
| 2001/0047154 | A1 | * | 11/2001 | Jepson ............... A61M 39/1011 604/167.01 |
| 2007/0251839 | A1 | | 11/2007 | Jessop et al. |
| 2013/0231616 | A1 | | 9/2013 | Fangrow et al. |

FOREIGN PATENT DOCUMENTS

| | | |
|---|---|---|
| JP | 2005-110873 A | 4/2005 |
| JP | 2010-517671 A | 5/2010 |
| JP | 2013-132349 A | 7/2013 |

OTHER PUBLICATIONS

Extended European Search Report dated Nov. 27, 2020 in counterpart European Patent Application No. 18771817.6.
International Searching Authority, "International Search Report," issued in connection with International Patent Application No. PCT/JP2018/010267, dated Apr. 17, 2018.
International Searching Authority, "Written Opinion," issued in connection with International Patent Application No. PCT/JP2018/010267, dated Apr. 17, 2018.

* cited by examiner

FEMALE SYRINGE AND SYRINGE KIT

CROSS-REFERENCE TO RELATED APPLICATIONS

This is a bypass continuation of PCT Application No. PCT/JP2018/010267, filed on Mar. 15, 2018, which claims priority to Japanese Application No. 2017-055227, filed on Mar. 22, 2017. The contents of these applications are hereby incorporated by reference in their entireties.

BACKGROUND

The present disclosure relates to a female syringe and a syringe kit.

A syringe kit for mixing two medicines—a first medicine in a first barrel and a second medicine in a second barrel—is disclosed, for example, in JP 2013-132349 A. This syringe kit is provided with a first barrel (barrel of a female syringe) including a connecting cylindrical portion provided with an inner tapered surface on an inner periphery and a male screw on an outer periphery, and a second barrel (barrel of a male syringe) including a nozzle portion provided with an outer tapered surface on an outer periphery that may be fitted to the inner tapered surface of the connecting cylindrical portion and a screw cylindrical portion having a female screw screwable with the male screw on an inner periphery. In the syringe kit, in order to mix the medicine in the first barrel and the medicine in the second barrel, the connection cylindrical portion of the first barrel and the screw cylindrical portion of the second barrel are connected by screwing.

SUMMARY

To inhibit liquid leakage in a connected state, the first barrel and the second barrel need to be strongly fitted. In the syringe kit disclosed in JP 2013-132349 A described above, a screwing portion of the connecting cylindrical portion of the first barrel and a screwing portion of the screw cylindrical portion of the second barrel are both screw-shaped, so that excessive screwing is possible. Therefore, there is a problem that the tapered surfaces are excessively fitted to each other, and the connection cylindrical portion (opening) of the first barrel is damaged or deformed, so that liquid tightness between the nozzle and the cylindrical portion is deteriorated. In addition, there is a problem that a distal end portion of either the first barrel or the second barrel is twisted to be damaged or deformed, and the liquid tightness between the nozzle and the cylindrical portion is deteriorated.

Embodiments of the present invention have been developed in consideration of such problems, and an object of certain embodiments is to provide a female syringe and a syringe kit capable of inhibiting damage and deformation of a barrel of a female syringe or a barrel of a male syringe due to excessive torque and inhibiting deterioration in liquid tightness between a nozzle and a cylindrical portion when screwing the barrel of the female syringe and the barrel of the male syringe with each other.

According to one embodiment, a female syringe includes a barrel including a hollow barrel body having an inner peripheral surface on which a gasket is slidable, a cylindrical portion extended in a distal end direction from a distal end of the barrel body into which a nozzle of a male syringe is insertable, and a projection with which a screw of a lock adapter of the male syringe is screwable; a hollow cylindrical packing made of an elastic material and arranged in the cylindrical portion to be integrated with the cylindrical portion; and a cap detachably attached to the cylindrical portion to close, in a liquid-tight manner, an opening of the packing. When the cap is detached from the cylindrical portion, the packing integrated with the cylindrical portion remains in the cylindrical portion, the opening is opened, and the nozzle of the male syringe is fittable in a liquid-tight manner to an inner side of the packing. At least in a state in which the cap is attached to the cylindrical portion and in a state in which the nozzle of the male syringe is fitted in a liquid-tight manner to the inner side of the packing, an outer peripheral surface of the packing is in close contact with an inner peripheral surface of the cylindrical portion so as to make a full circle of a liquid tight sealing portion in a circumferential direction of the cylindrical portion.

According to the female syringe having the above-described configuration, even when the cap is detached from the cylindrical portion of the barrel, the packing remains in the cylindrical portion. Then, when the projection and the lock adapter are screwed together to connect the female syringe and the male syringe, the nozzle is inserted into the cylindrical portion. As a result, the cylindrical portion and the nozzle are fitted in a liquid-tight manner via the packing. For this reason, damage and deformation of the barrel can be inhibited while securing good liquid tightness at the time of fitting.

The cap may include a base and a convex fitting portion projecting in a proximal end direction from the base, and the packing may be held over an entire circumference in a compressed state between the inner peripheral surface of the cylindrical portion and an outer peripheral surface of the convex fitting portion.

This configuration may ensure better liquid tightness.

The inner peripheral surface of the packing may include a first fitting surface to which the convex fitting portion is fitted and a second fitting surface having an inner diameter smaller than an inner diameter of the first fitting surface to which the nozzle of the male syringe is fittable formed on a proximal end side than the first fitting surface.

With this configuration, the inner diameter is set individually for the first fitting surface and the second fitting surface, so that the liquid tightness may be better secured in the cap attached (unopened) state and the male/female syringe fitted state.

A radially projecting engaging convex portion may be provided on one of the inner peripheral surface of the cylindrical portion and the outer peripheral surface of the packing, an engaging concave portion having a depth in a radial direction may be provided on the other of the inner peripheral surface of the cylindrical portion and the outer peripheral surface of the packing, and movement of the packing in an axial direction with respect to the cylindrical portion may be restricted by engagement between the engaging convex portion and the engaging concave portion.

As a result, removal of the packing from the cylindrical portion when the cap is opened may be realized by a simple configuration, and the packing may be surely left inside the cylindrical portion after the cap is opened.

The engaging concave portion may be provided on the outer peripheral surface of the packing.

By this configuration, the movement in the axial direction of the packing may be restricted without deteriorating rigidity of the cylindrical portion.

A distal end portion of the packing may be provided with the ring-shaped swelling portion projecting radially outward and is locked by the distal end surface of the cylindrical portion may be provided.

With this configuration, when the nozzle is fitted to the packing, the movement of the packing toward the barrel body may be surely inhibited.

According to another embodiment, a syringe kit includes: a male syringe including a barrel including a nozzle formed as a male lure and a lock adapter provided with a screw; and a female syringe including a barrel including a cylindrical portion into which the nozzle is insertable, and a projection with which the screw of the lock adapter is screwable, in which the female syringe is provided with a hollow cylindrical packing made of an elastic material and fitted in the cylindrical portion, and a cap detachably attached to the cylindrical portion to close, in a liquid-tight manner, an opening of the packing, and when the cap is detached from the cylindrical portion, the packing remains in the cylindrical portion, the opening is opened, and the nozzle of the male syringe is fittable in a liquid-tight manner to an inner side of the packing.

By this configuration, damage and deformation of the barrel of the female syringe can be inhibited while securing good liquid tightness at the time of fitting.

In the above-described syringe kit, the cylindrical portion may include a first cylindrical portion provided with the projection and has an outer diameter smaller than an inner diameter of the screw, and a second cylindrical portion formed adjacent to a proximal end side of the first cylindrical portion and having an outer diameter larger than the outer diameter of the first cylindrical portion, and the screw on a distal end portion of the lock adapter may fit to the second cylindrical portion in a state in which the fitting of the nozzle to the cylindrical portion via the packing is completed.

With this configuration, when the screw on the distal end portion of the lock adapter is fitted at the time of fitting, a fitting force stronger than that obtained by only fitting via packing may be obtained.

In the above-described syringe kit, in a state in which the fitting of the nozzle to the cylindrical portion via the packing is completed, the packing may be held between the cylindrical portion and the nozzle in a compressed state over an entire circumference.

This configuration provides better liquid tightness.

In the above-described syringe kit, the cylindrical portion may be provided with an abutment portion that restricts a fitting depth of the nozzle into the cylindrical portion by abutment of a distal end of the lock adapter when the nozzle is fitted to the cylindrical portion via the packing.

By this configuration, excessive fitting between the cylindrical portion and the nozzle may be effectively inhibited.

According to certain embodiments of the present invention, it is possible to inhibit damage and deformation of the barrel of the female syringe or the barrel of the male syringe due to excessive torque and inhibiting deterioration in liquid tightness between the nozzle and the cylindrical portion when screwing the barrel of the female syringe and the barrel of the male syringe with each other.

DETAILED DESCRIPTION

Embodiments of a female syringe and a syringe kit according to the present invention are described below with reference to the accompanying drawings.

Figure 1:
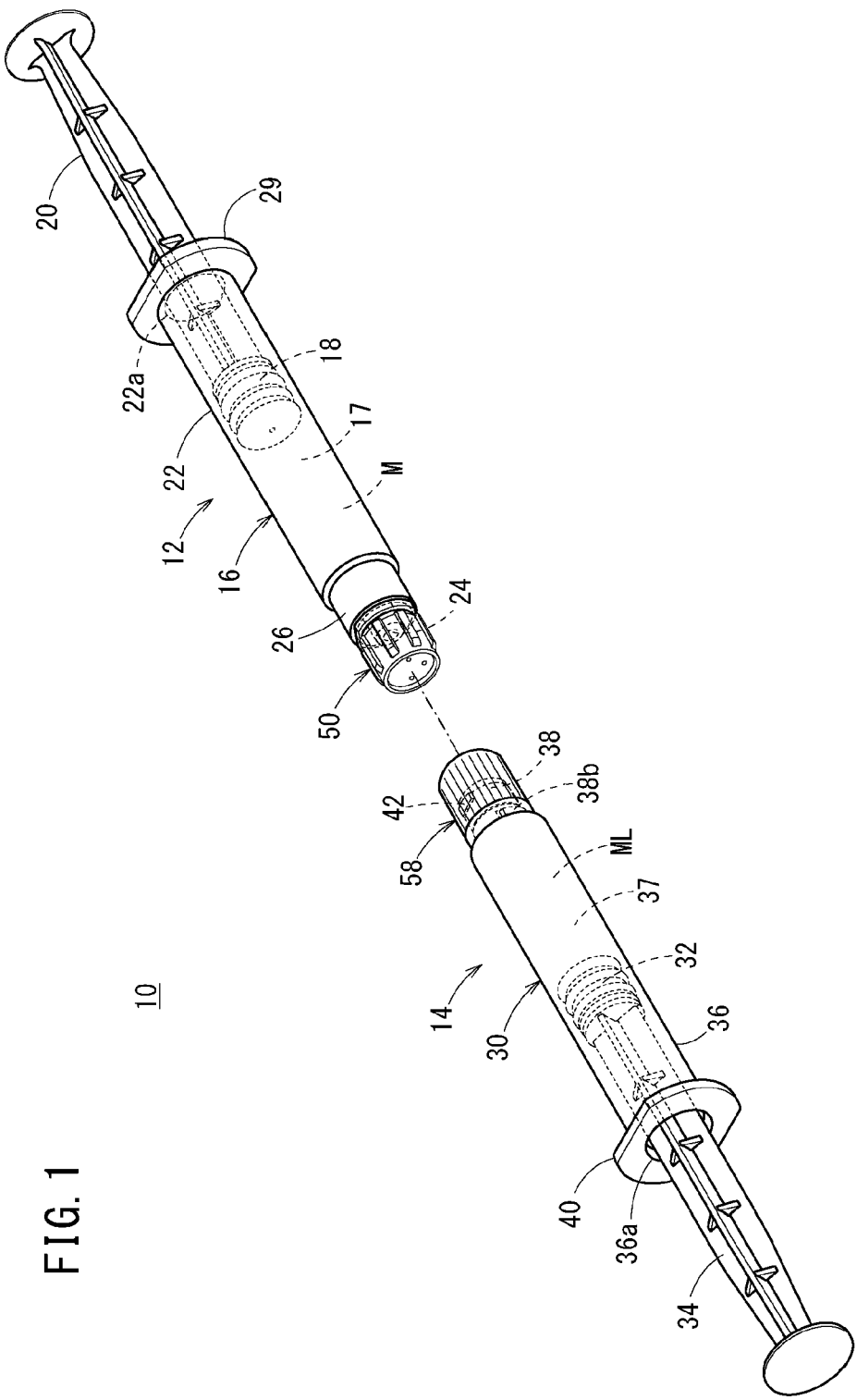
FIG. 1 is a perspective view of a syringe kit according to an embodiment of the present invention.

A syringe kit 10 according to this embodiment illustrated in FIG. 1 is a mixing kit for mixing a filling in one barrel and a filling in the other barrel. The syringe kit 10 is provided with a male syringe 12 and a female syringe 14 that may be screwed to be connected to each other. Both the male syringe 12 and the female syringe 14 are formed as prefilled syringes filled with contents such as medicine in advance.

Note that, in the following description, as for the male syringe 12, a side connected to the female syringe 14 or a direction thereof is referred to as a "distal end portion" or a "distal end direction", and the opposite side or the opposite direction is referred to as a "proximal end portion" or a "proximal end direction". Also, as for the female syringe 14, a side connected to the male syringe 12 or a direction thereof is referred to as a "distal end portion" or a "distal end direction", and the opposite side or the opposite direction is referred to as a "proximal end portion" or a "proximal end direction".

The male syringe 12 is provided with a barrel 16 (hereinafter abbreviated as a "male syringe barrel 16"), which is a hollow body, a cap 50 attached to the distal end portion of the male syringe barrel 16, a gasket 18 slidably inserted into the male syringe barrel 16, a pusher 20 connected to the gasket 18, and medicine M filled in a barrel chamber 17 formed of the barrel of the male syringe 16 and the gasket 18.

Figure 2:
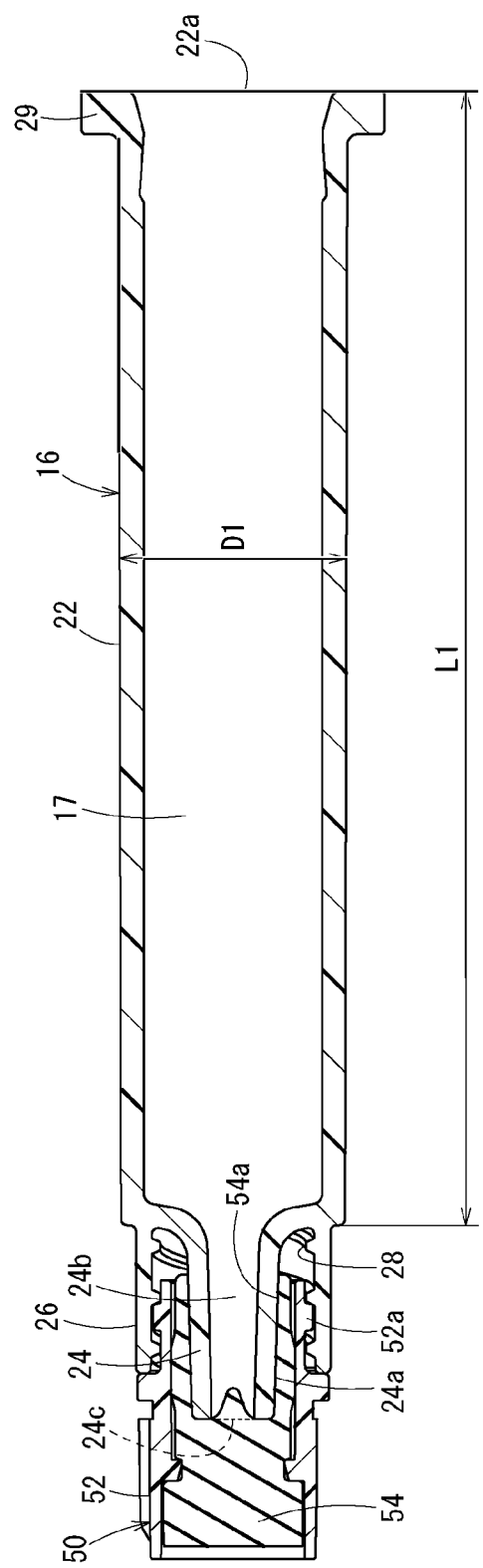
FIG. 2 is a cross-sectional view of a barrel of a male syringe.

As illustrated in FIG. 2, the male syringe barrel 16 includes a barrel body 22 having a substantially cylindrical shape on a proximal end of which a proximal end opening 22a is formed, a nozzle 24 provided on a distal end of the barrel body 22, a lock adapter 26 provided on an outer side of the nozzle 24, and a flange 29 formed so as to project radially outward from the proximal end of the barrel body 22. The barrel body 22, the nozzle 24, the lock adapter 26, and the flange 29 are integrally molded.

An outer diameter D1 of the barrel body 22 is not especially limited, but is preferably 6.7 mm or larger. Also, a length L1 in an axial direction of the barrel body 22 is not especially limited, but is preferably 35 mm or longer, and is more preferably 47 mm or longer. By setting the outer diameter D1 and the length L1 in the axial direction of the barrel body 22 in this manner, it is possible to easily screw while gripping the barrel body 22 when connecting the male syringe 12 to the female syringe 14.

The nozzle 24 extends from a central portion of the distal end of the barrel body 22 in the distal end direction such that a diameter thereof decreases with respect to the barrel body 22. The nozzle 24 includes a passage 24b that penetrates in the axial direction and is communicated with an inner cavity (barrel chamber 17) of the barrel body 22.

The nozzle 24 is formed as a male lure including a tapered outer peripheral surface 24a a cross-sectional outer shape of which is circular and an outer diameter of which decreases in the distal end direction. The nozzle 24 may be fitted in a cylindrical portion 38 (female lure) to be described later of the female syringe 14. The nozzle 24 projects in the distal end direction from a distal end surface of the lock adapter 26.

In FIG. 2, the lock adapter 26 is formed into a substantially hollow cylindrical shape that extends in the distal end direction from the distal end of the barrel body 22 and surrounds the nozzle 24 concentrically. A screw 28 is formed on an inner peripheral surface of the lock adapter 26.

In an initial state of the male syringe 12 illustrated in FIG. 1, the cap 50 is attached to the nozzle 24, and a distal end opening 24c of the nozzle 24 is sealed by the cap 50. The cap 50 is detached from the nozzle 24 when the male syringe 12 is used (when the syringe kit 10 is used).

As illustrated in FIG. 2, the cap 50 includes a hollow cap main body 52 made of a hard material and a sealing member 54 made of an elastic material attached to an inner side of the cap main body 52. A projection 52a which releasably engages with the screw 28 of the lock adapter 26 is formed on an outer peripheral portion of a proximal end of the cap main body 52.

The sealing member 54 is fixed to an inner peripheral portion of the cap main body 52. The sealing member 54 includes a sealing concave portion 54a opened in the proximal end direction and the nozzle 24 fits in the sealing concave portion 54a. In a state before usage in which the cap 50 is attached to the nozzle 24 (unopened state), the sealing member 54 is in close contact with the nozzle 24 in a liquid tight manner.

In FIG. 1, the gasket 18 is inserted into the barrel body 22 via the proximal end opening 22a that opens at the proximal end of the barrel body 22. The proximal end side of the barrel body 22 is sealed in a liquid tight manner by the gasket 18. The gasket 18 is made of, for example, an elastic material such as a rubber material. The gasket 18 is slidably arranged in the barrel body 22 with an outer peripheral portion in liquid tight contact with the inner peripheral surface of the barrel body 22.

The gasket 18 is connected to a distal end portion of the pusher 20. As a user pushes the pusher 20 in the axial direction (distal end direction or proximal end direction), the gasket 18 slides in the axial direction in the barrel body 22. Note that, the pusher 20 may also be connected to the gasket 18 when the male syringe 12 is used.

As long as the medicine M is dissolved/diluted/mixed by medical fluid ML (specifically, solution such as physiological saline) filled in the female syringe 14, this may be of any type such as powdered medicine, freeze-dried medicine, solid medicine, and liquid medicine. Such medicine M includes, for example, protein preparations, peptide preparations, antitumor agents, vitamins (multivitamins), various amino acids, antithrombotic agents such as heparin, insulin, antibiotics, analgesics, cardiotonic agents, intravenous injection anesthetics, medical narcotics, anti-parkinsonian agents, ulcer treatment agents, corticosteroids, arrhythmic agents and the like.

The female syringe 14 is provided with a barrel 30 (hereinafter abbreviated as a "female syringe barrel 30"), which is a hollow body, a packing 56 (refer to FIG. 3) arranged on an inner portion of the distal end of the female syringe 14, and a cap 58 attached to the distal end portion of the female syringe 14. The female syringe 14 is further provided with a gasket 32 slidably inserted into the female syringe barrel 30, a pusher 34 connected to the gasket 32, and the medical fluid ML filled in a barrel chamber 37 formed of the barrel of the female syringe 30 and the gasket 32.

Figure 3:
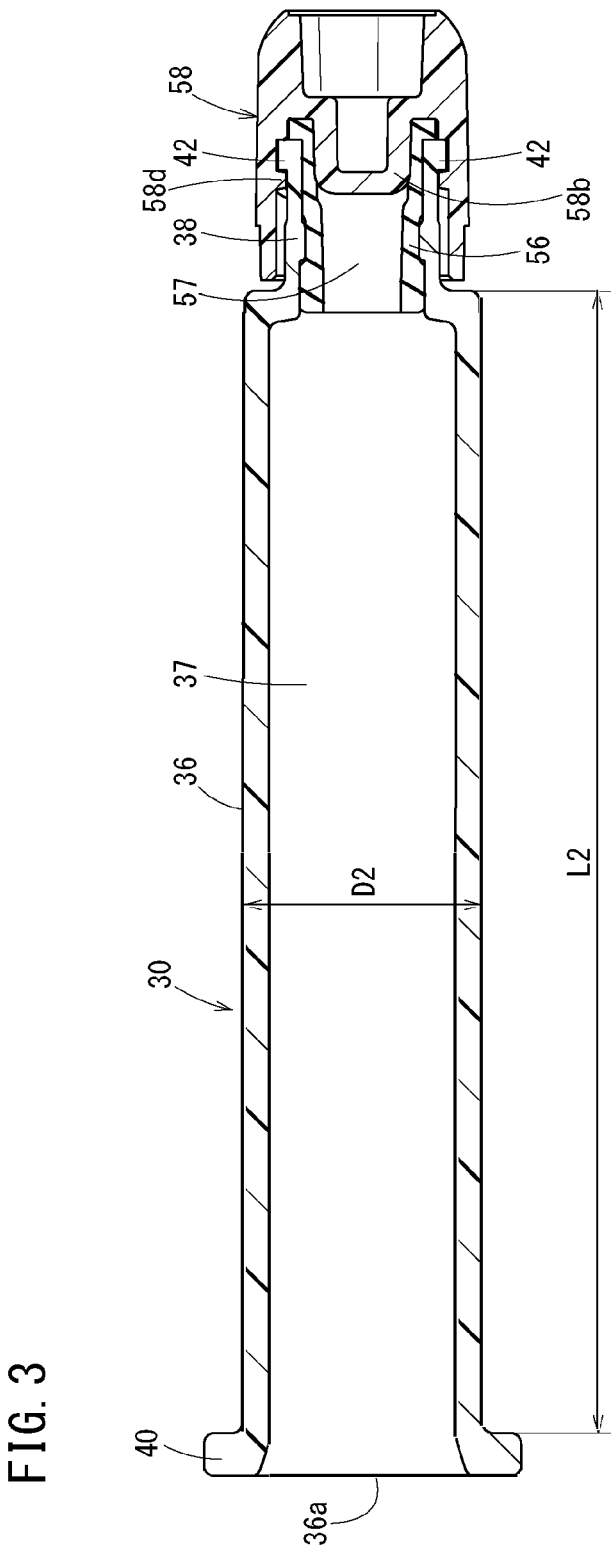
FIG. 3 is a cross-sectional view of a barrel of a female syringe.

As illustrated in FIG. 3, the female syringe barrel 30 includes a barrel body 36 having a substantially cylindrical shape and having a proximal end opening 36a formed on a proximal end thereof, a cylindrical portion 38 projecting in the distal end direction from a distal end of the barrel body 36, and a flange 40 formed so as to project radially outward from the proximal end of the barrel body 36. The barrel body 36, the cylindrical portion 38, and the flange 40 are integrally molded. Note that, although the cylindrical portion 38 is smaller than the barrel body 36 in FIG. 3, the cylindrical portion 38 may be of the same size as that of the barrel body 36 or may be larger than the barrel body 36.

An outer diameter D2 of the barrel body 36 is not especially limited, but is preferably 6.7 mm or larger. Also, a length L2 in an axial direction of the barrel body 36 is not especially limited, but is preferably 35 mm or longer, and is more preferably 47 mm or longer. By setting the outer diameter D2 and the length L2 in the axial direction of the barrel body 36 in this manner, it is possible to easily screw while gripping the barrel body 36 when connecting the female syringe 14 to the male syringe 12.

The cylindrical portion 38 extends from a central portion of the distal end of the barrel body 36 in the distal end direction such that a diameter thereof decreases with respect to the barrel body 36. The cylindrical portion 38 has a substantially cylindrical shape penetrating in the axial direction. The nozzle 24 (refer to FIG. 2) of the male syringe 12 may be inserted into the cylindrical portion 38.

Figure 4:
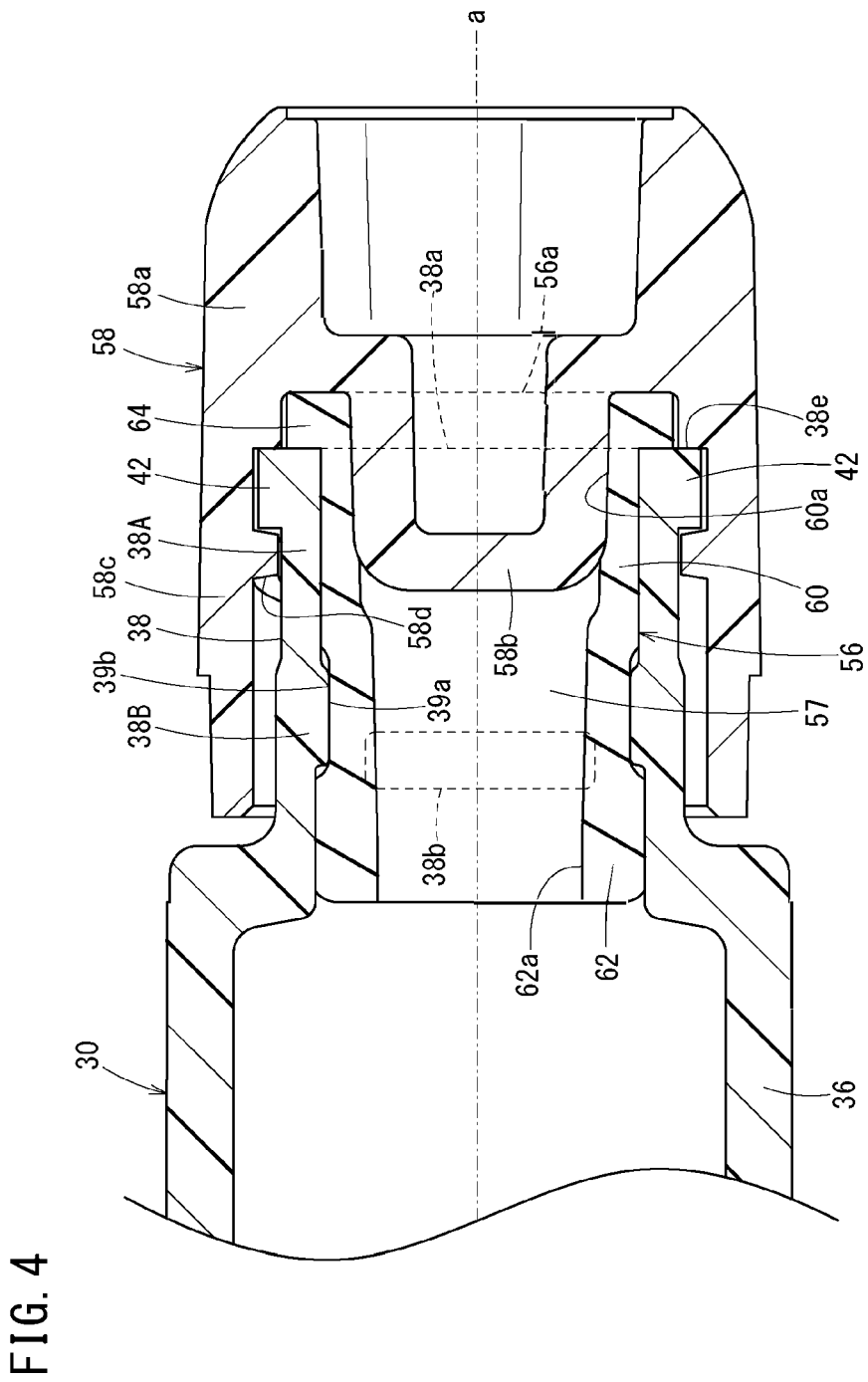
FIG. 4 is a cross-sectional view of a distal end portion of a female syringe.
Figure 5:
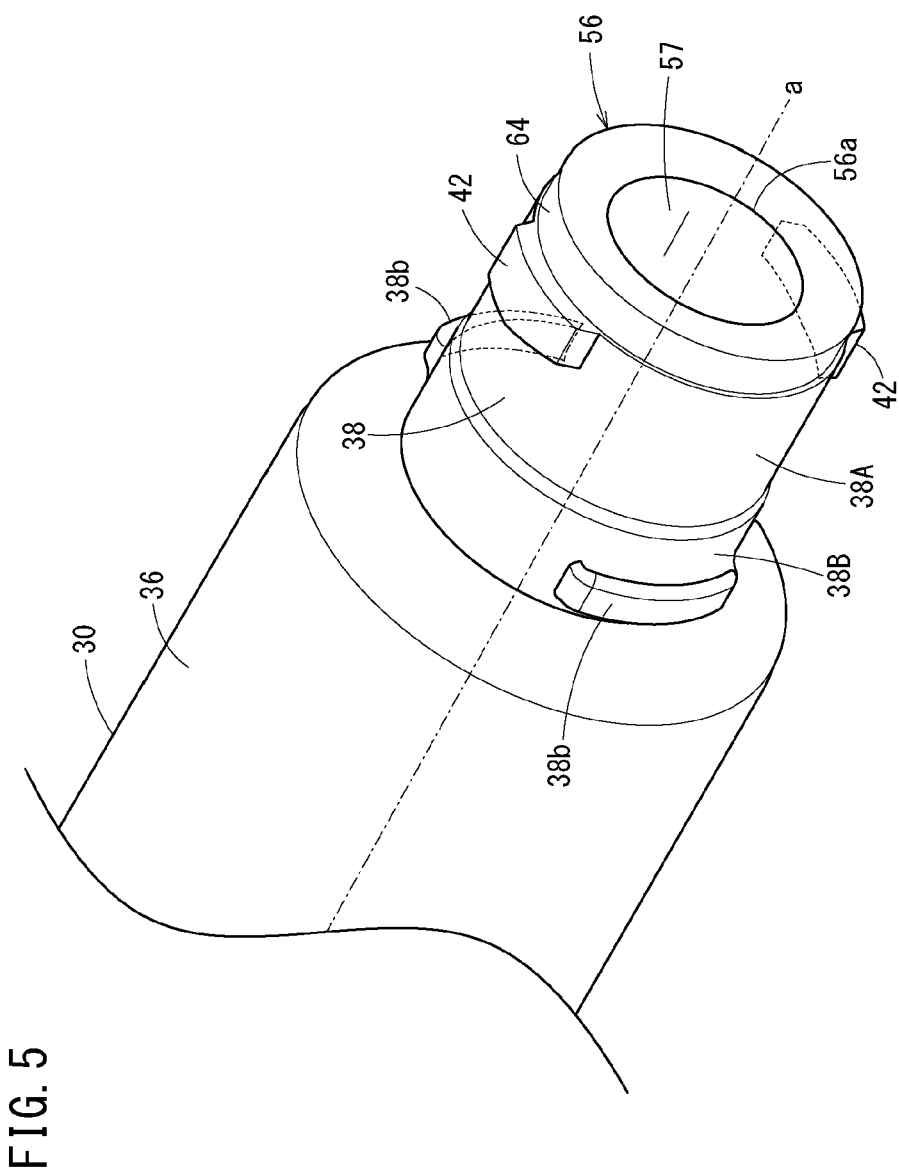
FIG. 5 is a perspective view of a distal end portion of the barrel of the female syringe.

As illustrated in FIGS. 4 and 5, on an outer peripheral portion of a distal end of the cylindrical portion 38, two projections 42 projecting outward (radially outward) in opposite directions with respect to an axis a (center line) of the cylindrical portion 38 are provided. The two projections 42 may be screwed with the screw 28 (refer to FIG. 2) provided on the lock adapter 26 of the male syringe barrel 16.

The cylindrical portion 38 includes a first cylindrical portion 38A provided with the projections 42 and having an outer diameter smaller than an inner diameter of the screw 28, and a second cylindrical portion 38B formed so as to be adjacent to a proximal end side of the first cylindrical portion 38A and having an outer diameter larger than the outer diameter of the first cylindrical portion 38A. The first cylindrical portion 38A forms a distal end side of the cylindrical portion 38. The second cylindrical portion 38B forms a proximal end side of the cylindrical portion 38.

As illustrated in FIG. 4, an engaging convex portion 39a projecting radially inward is provided on an inner peripheral surface of the cylindrical portion 38. The engaging convex portion 39a is formed into an annular shape to make a full circle in a circumferential direction. The engaging convex portion 39a is provided on the second cylindrical portion 38B. A projecting height of the engaging convex portion 39a from the inner peripheral surface of the cylindrical portion 38 is shorter than a thickness of the cylindrical portion 38. Note that, the engaging convex portion 39a may be formed in a range smaller than a full circle in the circumferential direction, or a plurality of the same may be formed at intervals in the circumferential direction. The engaging convex portion 39a may also be provided on the first cylindrical portion 38A or may be provided across the first cylindrical portion 38A and the second cylindrical portion 38B.

As illustrated in FIG. 5, on an outer peripheral surface of the cylindrical portion 38, an abutment portion 38b is provided for restricting a fitting depth of the nozzle 24 (refer to FIG. 2) into the cylindrical portion 38. Specifically, the abutment portion 38b projects radially outward from an outer peripheral surface of the second cylindrical portion 38B and extends in the circumferential direction. In FIG. 5, two abutment portions 38b are arranged on opposite sides with respect to the axis a of the cylindrical portion 38. In a state in which the cap 58 is attached to the cylindrical portion 38 (cap unopened state) as illustrated in FIG. 4, the abutment portion 38b is covered with the cap 58 and fitted to an inner peripheral surface of the cap 58.

The packing 56 is arranged in the cylindrical portion 38 and is integrated with the cylindrical portion 38. In FIG. 4, the packing 56 is fitted in the cylindrical portion 38 and is in close contact with the inner peripheral surface of the cylindrical portion 38 in a liquid tight manner over an entire circumference. The packing 56 is a hollow cylindrical member made of an elastic material and having an inner cavity 57 penetrating in the axial direction. The packing 56 is held between the inner peripheral surface of the cylindrical portion 38 and an outer peripheral surface of a convex fitting portion 58b to be described later of the cap 58 in a compressed state over the entire circumference. Note that the packing 56 may also be integrated with the cylindrical portion 38 by bonding, welding, two-color molding or the like.

At least in a state in which the cap 58 is attached to the cylindrical portion 38 and in a state in which the nozzle 24 of the male syringe 12 fits in the inner side of the packing 56 in a liquid tight manner, the outer peripheral surface of the packing 56 is in close contact with the inner peripheral surface of the cylindrical portion 38 so as to make a full circle of a liquid tight sealing portion in the circumferential direction of the cylindrical portion 38. Note that, in a state in which the cap 58 is detached from the cylindrical portion 38 and in a state in which the nozzle 24 of the male syringe 12 is not inserted into the packing 56, the outer peripheral surface of the packing 56 is not required to be in close contact with the inner peripheral surface of the cylindrical portion 38.

The packing 56 is provided with a first peripheral wall portion 60 including a first fitting surface 60a to which the convex fitting portion 58b is fitted in the unopened state of the cap 58 and a second peripheral wall portion 62 including a second fitting surface 62a formed on the proximal end side than the first fitting surface 60a. The first fitting surface 60a forms a distal end side area of the inner peripheral surface of the packing 56. As illustrated in FIG. 6B, the first fitting surface 60a is formed into a tapered shape an outer diameter of which decreases in the proximal end direction. Note that the first fitting surface 60a may also be formed into a straight shape having a constant outer diameter in the axial direction.

The second fitting surface 62a forms a proximal end side area of the inner peripheral surface of the packing 56. The second fitting surface 62a has an inner diameter smaller than an inner diameter of the first fitting surface 60a, and the nozzle 24 (refer to FIG. 2) of the male syringe 12 may be fitted thereto. A step is formed between the first fitting surface 60a and the second fitting surface 62a. The second fitting surface 62a is formed into a tapered shape (female lure) an outer diameter of which decreases in the proximal end direction. Note that the second fitting surface 62a may also be formed into a straight shape having a constant outer diameter in the axial direction.

Figure 6A:
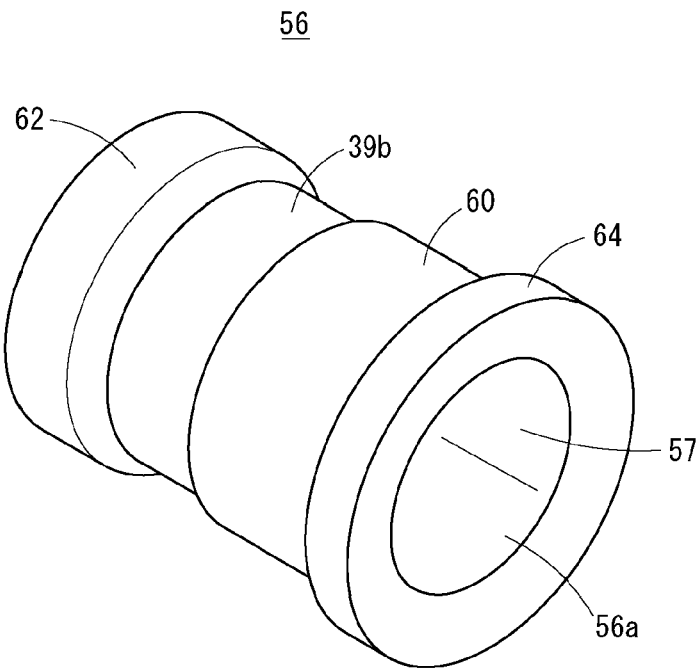
FIG. 6A is a perspective view of a packing.
Figure 6B:
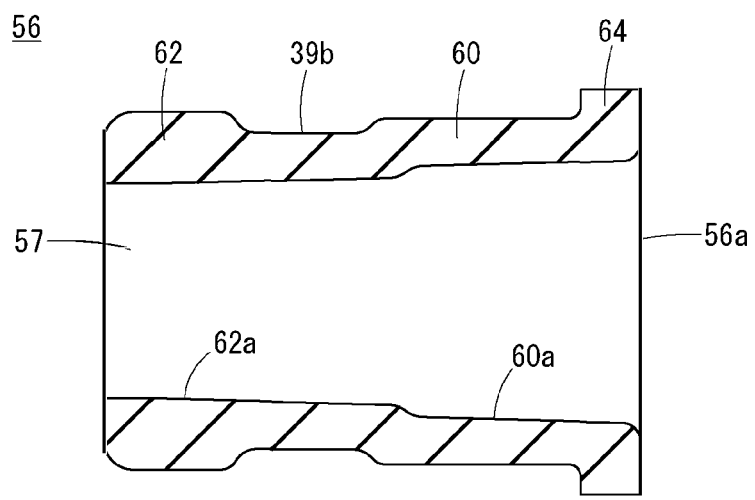
FIG. 6B is a cross-sectional view of the packing.

As illustrated in FIGS. 6A and 6B, the outer peripheral surface of the packing 56 is provided with an engaging concave portion 39b having a depth in the radial direction. The engaging concave portion 39b is formed into an annular shape that makes a full circle in the circumferential direction. The engaging concave portion 39b is provided on an outer peripheral surface of the second peripheral wall portion 62 (a position surrounding the second fitting surface 62a). As illustrated in FIG. 4, the engaging convex portion 39a provided on the cylindrical portion 38 engages with the engaging concave portion 39b. Movement of the packing 56 in the axial direction with respect to the cylindrical portion 38 is restricted by the engagement of the engaging convex portion 39a with the engaging concave portion 39b.

Note that, the engaging concave portion 39b may be formed in a range smaller than a full circle in the circumferential direction, or a plurality of the same may be formed at intervals in the circumferential direction. It is also possible that an engaging convex portion which projects radially outward is provided on the outer peripheral surface of the packing 56, an engaging concave portion having a depth in the radial direction is provided on the inner peripheral surface of the cylindrical portion 38, and the engaging convex portion and the engaging concave portion engage with each other unlike the configuration illustrated in FIG. 4 and the like.

A ring-shaped swelling portion 64 projecting radially outward is provided on a distal end portion of the packing 56 (a distal end portion of the first peripheral wall portion 60). In a state in which the cap 58 is attached to the cylindrical portion 38, the ring-shaped swelling portion 64 is held between a distal end surface 38e of the cylindrical portion 38 and a base 58a of the cap 58 in the axial direction, and is in close contact with the distal end surface 38e and the base 58a in a full circle in a liquid tight manner.

As an elastic material of the packing 56, there may be, for example, various rubber materials such as natural rubber, butyl rubber, isoprene rubber, butadiene rubber, styrene-butadiene rubber, and silicone rubber, various thermoplastic elastomers such as a polyurethane type, a polyester type, a polyamide type, an olefin type, and a styrene type, or a mixture thereof.

In an initial state of the female syringe 14 illustrated in FIG. 1, the cap 58 is attached to the cylindrical portion 38. The cap 58 is detached from the cylindrical portion 38 when the female syringe 14 is used (when the syringe kit 10 is used).

In FIG. 4, the cap 58 closes the distal end opening 56a of the packing 56 in a liquid tight manner. As a result, the cap 58 closes the distal end opening 38a of the cylindrical portion 38 in a liquid tight manner via the packing 56. The cap 58 covers the cylindrical portion 38 and detachably engages with the projection 42. Specifically, the cap 58 includes the base 58a, the convex fitting portion 58b projecting in the proximal end direction from the base 58a, and a cylindrical cover portion 58c that surrounds the convex fitting portion 58b and projects in the proximal end direction from the base 58a.

The base 58a forms a distal end portion of the cap 58. The convex fitting portion 58b is formed into a cylindrical shape that projects in the proximal end direction from a central portion of the base 58a. The outer peripheral portion of the convex fitting portion 58b is formed into a tapered shape an outer diameter of which decreases in the proximal end direction. Note that the outer peripheral portion of the convex fitting portion 58b may also be formed into a straight shape having a constant outer diameter in the axial direction.

In a state in FIG. 4 in which the cap 58 is attached to the cylindrical portion 38, the convex fitting portion 58b fits to the first fitting surface 60a of the packing 56 but does not fit to the second fitting surface 62a, and the outer peripheral surface of the convex fitting portion 58b is in close contact with the first fitting surface 60a over the entire circumference.

The cylindrical cover portion 58c projects in the proximal end direction from the convex fitting portion 58b. The cylindrical cover portion 58c is formed into a substantially cylindrical shape. A screw 58d is formed on an inner peripheral surface of the cylindrical cover portion 58c. In FIG. 4, the screw 58d engages with the projection 42 provided on the cylindrical portion 38. A most proximal end portion 58de of the screw 58d is located on the proximal end side (opening 58f side of the cap 58) than a proximal end surface 58be of the convex fitting portion 58b (refer to FIG. 7).

The cap 58 is formed of a material harder than that of the packing 56 (for example, selected from those exemplified below as components of the male syringe barrel 16 and the female syringe barrel 30).

In FIG. 1, the gasket 32 is inserted into the barrel body 36 via the proximal end opening 36a that opens at the proximal end of the barrel body 36. The gasket 32 seals the proximal end of the barrel body 36 in a liquid tight manner. The gasket 32 is formed of, for example, an elastic material such as a rubber material. The gasket 32 is slidably arranged in the barrel body 36 with an outer peripheral portion in liquid tight contact with the inner peripheral surface of the barrel body 36.

The gasket 32 is connected to a distal end portion of the pusher 34. When the user pushes the pusher 34 in the axial direction (distal end direction or proximal end direction), the gasket 32 slides in the axial direction in the barrel body 36. Note that, the pusher 34 may be connected to the gasket 32 when the female syringe 14 is used.

The medical fluid ML is fluid capable of dissolving, diluting, or mixing the medicine M in the male syringe 12. Such medical fluid ML may be medicine solvent such as physiological saline, medicine diluent, medicine mixture, or medicine solution containing medicine (for example, vitamins and minerals). Note that, it is sufficient that the medical fluid ML is not filled in advance in the female syringe 14 as in this embodiment but sucked by a required amount from a vial or the like into the empty female syringe 14 as necessary.

In this embodiment, the male syringe barrel 16 and the female syringe barrel 30 are both made of cyclic polyolefin having high rigidity and high toughness. Note that the male syringe barrel 16 and female syringe barrel 30 may be made of polypropylene, polyethylene, polystyrene, polyamide, polycarbonate, polyvinyl chloride, poly-(4-methylpentene-1), acrylic resin, acrylonitrile-butadiene-styrene copolymer, polyester such as polyethylene terephthalate and the like.

Next, a method of using the syringe kit 10 configured as described above is described.

Figure 7:
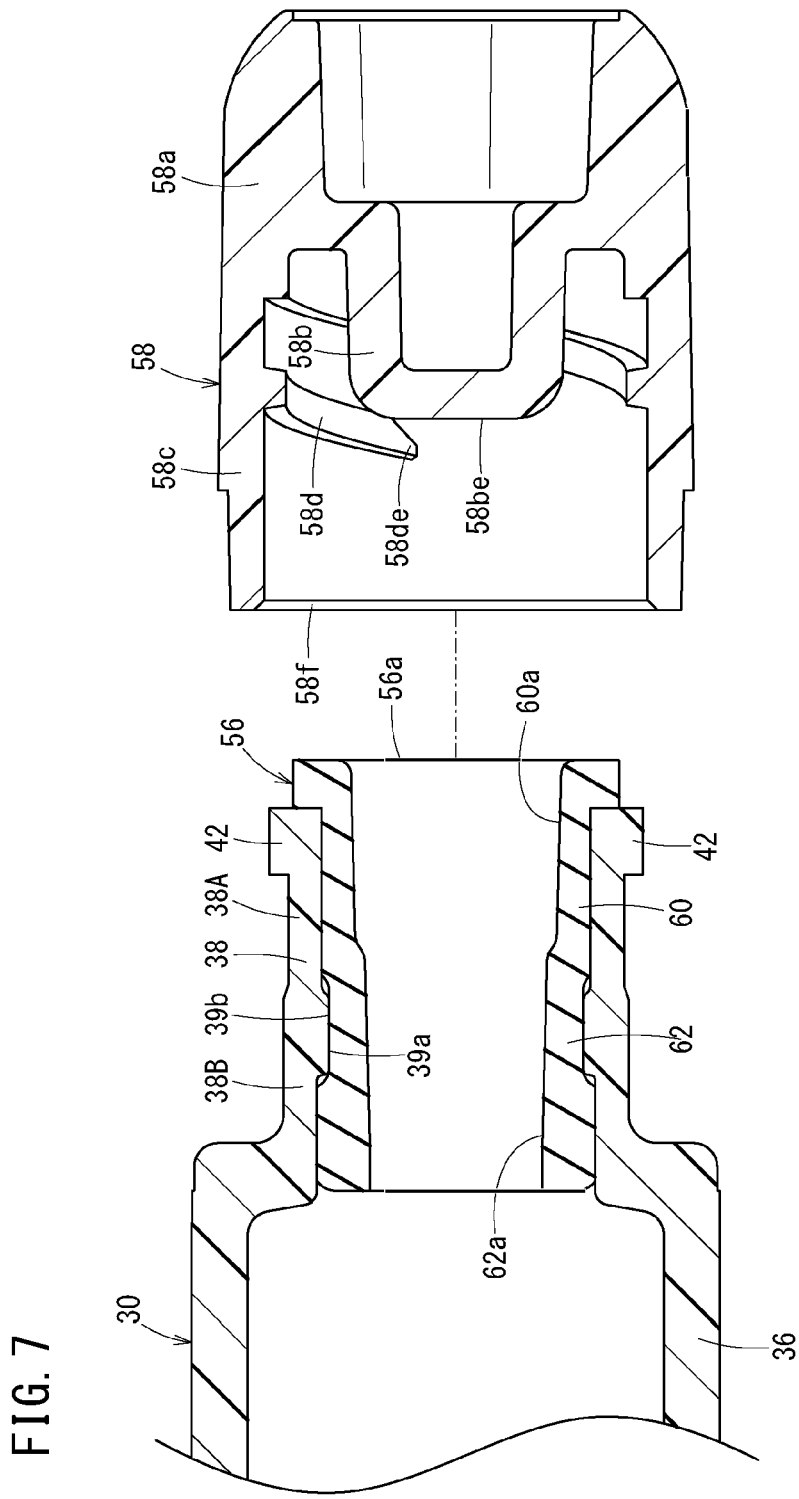
FIG. 7 is a cross-sectional view of a state in which a cap is detached from a cylindrical portion of the barrel of the female syringe.

First, in the male syringe 12 and female syringe 14 illustrated in FIG. 1, the cap 50 is detached from the nozzle 24 of the male syringe barrel 16 and the cap 58 is detached from the cylindrical portion 38 of the female syringe barrel 30 (opened). When the cap 58 is detached from the cylindrical portion 38, as illustrated in FIG. 7, the packing 56 remains in the cylindrical portion 38, and the distal end opening 56a of the packing 56 is opened. That is, since the packing 56 is fixed to the cylindrical portion 38 by the engagement between the engaging convex portion 39a and the engaging concave portion 39b, the packing 56 is separated from the cap 58 (convex fitting portion 58b) along with the removal of the cap 58 from the cylindrical portion 38.

Figure 8:
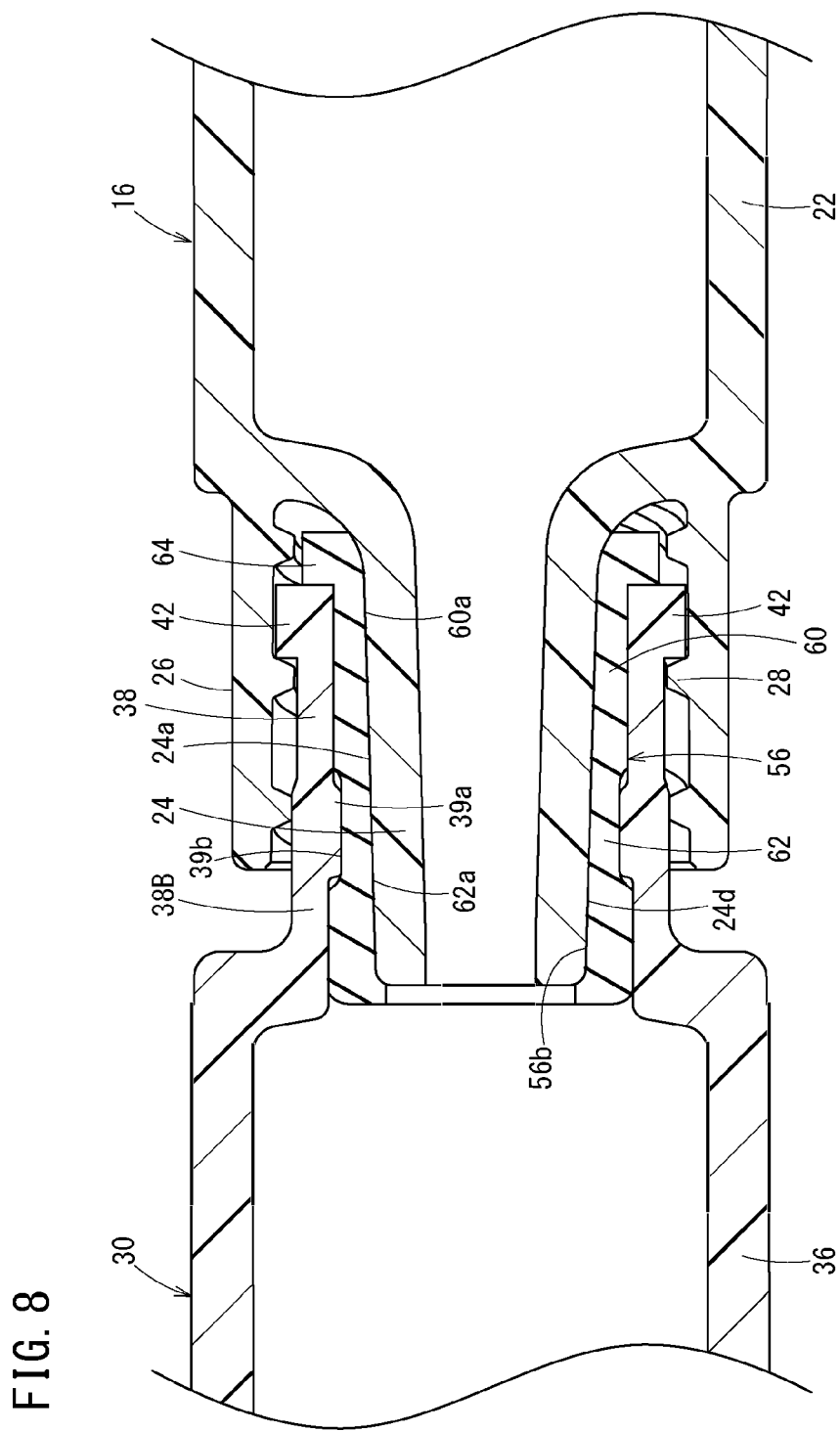
FIG. 8 is a cross-sectional view of a state in which the male syringe and the female syringe are connected.

Next, as illustrated in FIG. 8, the male syringe barrel 16 and the female syringe barrel 30 are connected to each other. Specifically, the screw 28 of the lock adapter 26 and the projection 42 provided on the cylindrical portion 38 of the female syringe barrel 30 are screwed together. Along with this screwing, the nozzle 24 of the male syringe barrel 16 is inserted into the cylindrical portion 38 of the female syringe barrel 30 and the packing 56. As a result, the packing 56 is held between the cylindrical portion 38 and the nozzle 24 in a compressed state, the inner peripheral surface of the packing 56 is brought into close contact with the tapered outer peripheral surface 24a of the nozzle 24 in a liquid tight manner over the entire circumference, and the outer peripheral surface of the packing 56 is brought into close contact with the inner peripheral surface of the cylindrical portion 38 in a liquid tight manner over the entire circumference.

Next, the medical fluid ML and the medicine M are mixed by performing a pumping operation using the pusher 20 of the male syringe 12 and the pusher 34 of the female syringe 14. Specifically, the medical fluid ML is injected from the female syringe barrel 30 into the male syringe barrel 16 by pushing the pusher 34 of the female syringe 14 toward the female syringe 14, and the medical fluid ML is mixed with the medicine M in the male syringe barrel 16. Next, the pusher 20 of the male syringe 12 is pushed toward the male syringe 12 to inject the mixture (the mixture of the medical fluid ML and the medicine M) from the male syringe barrel 16 into the female syringe barrel 30. Then, by repeating such movement of the mixture several times between the male syringe barrel 16 and the female syringe barrel 30, dissolution, dilution or mixing of the medicine M is promoted, and desired medicine solution is prepared.

In this case, according to this embodiment, the female syringe 14 is provided with the hollow cylindrical packing 56 arranged in the cylindrical portion 38 and is integrated with the cylindrical portion 38, and the cap 58 that covers the cylindrical portion 38 and closes the distal end opening 56a of the packing 56 in a liquid tight manner. Then, when the cap 58 is detached from the cylindrical portion 38, the packing 56 integrated with the cylindrical portion 38 remains in the cylindrical portion 38, the distal end opening 56a is opened, and the nozzle 24 may be fit in a liquid-tight manner to the inner side of the packing 56. For this reason, even when the cap 58 is detached from the cylindrical portion 38 of the female syringe barrel 30, the packing 56 remains in the cylindrical portion 38. Then, when the projection 42 and the lock adapter 26 are screwed together to connect the female syringe barrel 30 and the male syringe barrel 16, the nozzle 24 is inserted into the cylindrical portion 38. As a result, the cylindrical portion 38 and the nozzle 24 are fitted in a liquid-tight manner via the packing 56. Therefore, damage and deformation of the female syringe barrel 30 may be inhibited while securing good liquid tightness at the time of fitting.

The cap 58 includes the base 58a and the convex fitting portion 58b projecting in the proximal end direction from the base 58a, and before opening the cap 58, the packing 56 is held between the inner peripheral surface of the cylindrical portion 38 and the outer peripheral surface of the convex fitting portion 58b over an entire circumference in a compressed state. This configuration may ensure better liquid tightness.

The inner peripheral surface of the packing 56 includes the first fitting surface 60a to which the convex fitting portion 58b is fitted and the second fitting surface 62a having the inner diameter smaller than the inner diameter of the first fitting surface 60a formed on the proximal end side than the first fitting surface 60a to which the nozzle 24 of the male syringe 12 may be fitted. With this configuration, the inner diameter is set individually for the first fitting surface 60a and the second fitting surface 62a, so that the liquid tightness may be better secured in the cap attached (unopened) state and the male/female syringe fitted state.

In this case, the second peripheral wall portion 62 having the second fitting surface 62a is held between the cylindrical portion 38 and the nozzle 24 in a compressed state. Therefore, a liquid tight seal is formed over the entire circumference between a distal end portion outer peripheral surface 24d of the nozzle 24 and the packing 56, and a liquid tight seal is formed over the entire circumference between a proximal end portion outer peripheral surface 56b of the packing 56 and the female syringe barrel 30. Therefore, the liquid tightness in the fitting state between the cylindrical portion 38 and the nozzle 24 may be better secured.

In one of the inner peripheral surface of the cylindrical portion 38 and the outer peripheral surface of the packing 56, a radially projecting engaging convex portion 39a is provided, and on the other of the inner peripheral surface of the cylindrical portion 38 and the outer peripheral surface of the packing 56, the engaging concave portion 39b having a depth in the radial direction is provided. Then, movement of the packing 56 in the axial direction with respect to the cylindrical portion 38 is restricted by the engagement of the engaging convex portion 39a with the engaging concave portion 39b. As a result, removal of the packing 56 from the cylindrical portion 38 when the cap 58 is opened may be realized by a simple configuration, and the packing 56 may be surely left inside the cylindrical portion 38 after the cap 58 is opened.

In a case of this embodiment, the engaging concave portion 39b is provided on the outer peripheral surface of the packing 56. By this configuration, the movement in the axial direction of the packing 56 may be restricted without deteriorating rigidity of the cylindrical portion 38.

On the distal end portion of the packing 56, the ring-shaped swelling portion 64 that projects radially outward and is locked by the distal end surface 38e of the cylindrical portion 38 is provided. Therefore, when the nozzle 24 is fitted to the packing 56, the movement of the packing 56 toward the barrel body 36 may be surely inhibited.

The cylindrical portion 38 includes a first cylindrical portion 38A provided with the projections 42 and having an outer diameter smaller than an inner diameter of the screw 28, and a second cylindrical portion 38B formed so as to be adjacent to a proximal end side of the first cylindrical portion 38A and having an outer diameter larger than the outer diameter of the first cylindrical portion 38A. Then, as illustrated in FIG. 8, in a state in which the fitting of the nozzle 24 to the cylindrical portion 38 via the packing 56 is completed, the screw 28 on the distal end portion of the lock adapter 26 is fitted to the second cylindrical portion 38B. With this configuration, when the screw 28 on the distal end portion of the lock adapter 26 is fitted at the time of fitting, a fitting force stronger than that only the fitting via the packing 56 may be obtained.

Figure 9:
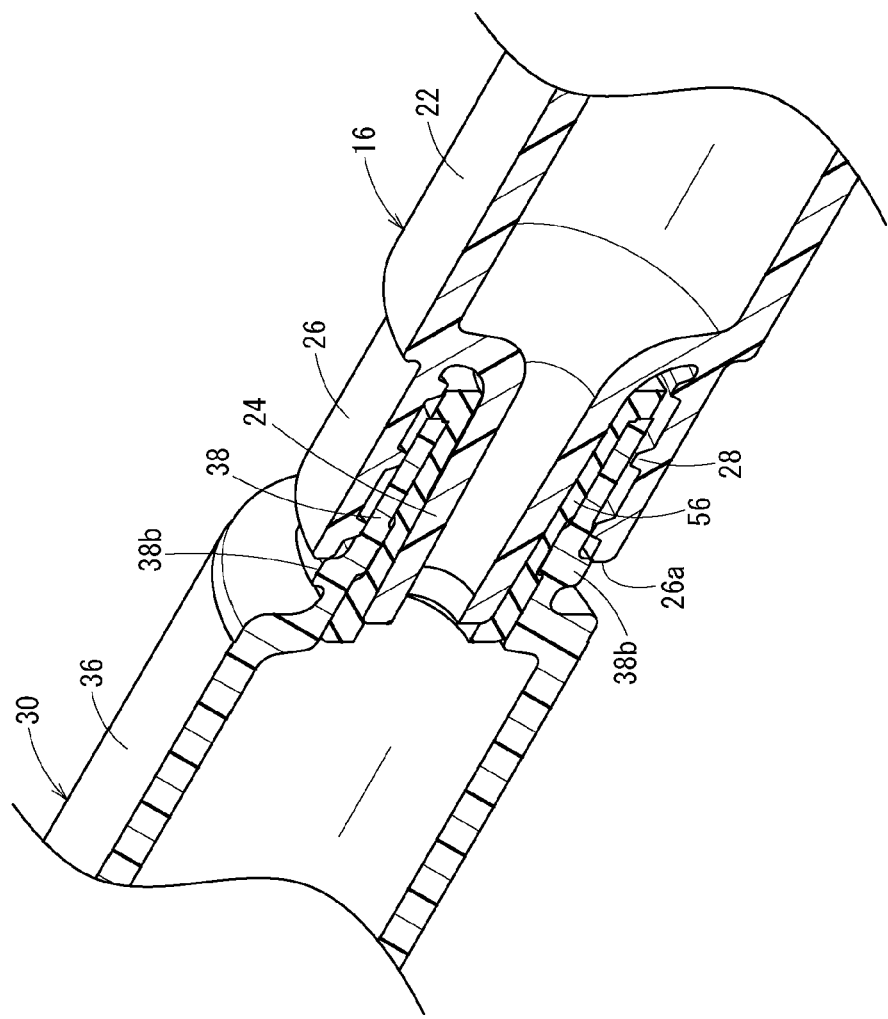
FIG. 9 is a perspective view of a state in which the male syringe and the female syringe are connected.

As illustrated in FIG. 9, the abutment portion 38b provided on the cylindrical portion 38 restricts the fitting depth of the nozzle 24 into the cylindrical portion 38 because the distal end 26a of the lock adapter 26 abuts when the nozzle 24 is fitted to the cylindrical portion 38 via the packing 56.

Therefore, excessive fitting between the cylindrical portion 38 and the nozzle 24 may be effectively inhibited.

In the above-described syringe kit 10, the outer diameter D1 of the barrel body 22 of the male syringe barrel 16 and the outer diameter D2 of the barrel body 36 of the female syringe barrel 30 may be both 6.7 mm or larger, and the length in the axial direction of the barrel body 22 of the male syringe barrel 16 and the length in the axial direction of the barrel body 36 of the female syringe barrel 30 may be both 35 mm or longer.

In general, a barrel for a syringe including a barrel body with such an outer dimension is likely to be subjected to strong torque at the time of screwing and is easily broken or deformed; however, the present invention in which breakage or deformation of the cylindrical portion 38 may be inhibited and deterioration in the liquid tightness between the nozzle 24 and the cylindrical portion 38 may be effectively inhibited is useful.

The present invention is not limited to the above-described embodiment, and various modifications may be made without departing from the scope of the present invention.

The contents of the male syringe 12 and the contents of the female syringe 14 may be opposite to those in the embodiment described above. That is, the male syringe 12 may be filled with the medical fluid ML and the female syringe 14 may be filled with the medicine M.

The invention claimed is:

1. A female syringe comprising:
   a female syringe barrel comprising:
   a hollow barrel body having an inner peripheral surface on which a gasket is slidable,
   a cylindrical portion extended in a distal end direction from a distal end of the barrel body, into which a nozzle of a male syringe is insertable, and
   a projection with which a screw of a lock adapter of the male syringe is screwable;
   a hollow cylindrical packing made of an elastic material and arranged in the cylindrical portion, wherein the hollow cylindrical packing comprises an opening that extends entirely through the hollow cylindrical packing from a distal end to a proximal end of the hollow cylindrical packing; and
   a cap detachably attached to the cylindrical portion and configured to close, in a liquid-tight manner, the opening of the packing;
   wherein the female syringe is configured such that, when the cap is detached from the cylindrical portion, the packing remains in the cylindrical portion, the opening is opened, and the nozzle of the male syringe is fittable in a liquid-tight manner to an inner side of the packing; and
   at least in a state in which the cap is attached to the cylindrical portion and in a state in which the nozzle of the male syringe is fitted in a liquid-tight manner to the inner side of the packing, an outer peripheral surface of the packing is in close contact with an inner peripheral surface of the cylindrical portion so as to make a full circle of a liquid tight sealing portion in a circumferential direction of the cylindrical portion.

2. The female syringe according to claim 1, wherein:
   the cap comprises:
   a base, and
   a convex fitting portion projecting in a proximal end direction from the base; and
   the packing is held between the inner peripheral surface of the cylindrical portion and an outer peripheral surface of the convex fitting portion in a compressed state over an entire circumference of the packing.

3. The female syringe according to claim 2, wherein:
an inner peripheral surface of the packing comprises:
   a first fitting surface to which the convex fitting portion is fitted, and
   a second fitting surface to which the nozzle of the male syringe is fittable, wherein the second fitting surface is formed on a proximal end side of the first fitting surface, and wherein an inner diameter of the second fitting surface is smaller than an inner diameter of the first fitting surface.

4. The female syringe according to claim 1, wherein:
a radially projecting engaging convex portion is provided on one of the inner peripheral surface of the cylindrical portion and the outer peripheral surface of the packing;
an engaging concave portion having a depth in a radial direction is provided on the other of the inner peripheral surface of the cylindrical portion and the outer peripheral surface of the packing; and
movement of the packing in an axial direction with respect to the cylindrical portion is restricted by engagement between the engaging convex portion and the engaging concave portion.

5. The female syringe according to claim 4, wherein:
the engaging concave portion is provided on the outer peripheral surface of the packing.

6. The female syringe according to claim 1, wherein:
a distal end portion of the packing comprises a ring-shaped swelling portion projecting radially outward and is locked by a distal end surface of the cylindrical portion.

7. A syringe kit comprising:
a male syringe comprising a male syringe barrel comprising:
   a nozzle formed as a male lure, and
   a lock adapter comprising a screw; and
a female syringe including a female syringe barrel for comprising:
   a cylindrical portion into which the nozzle is insertable, and
   a projection with which the screw of the lock adapter is screwable;
wherein the female syringe comprises:
   a hollow cylindrical packing made of an elastic material and fitted in the cylindrical portion, and
   a cap detachably attached to the cylindrical portion to close, in a liquid-tight manner, an opening of the packing; and
wherein the syringe kit is configured such that, when the cap is detached from the cylindrical portion, the packing remains in the cylindrical portion, the opening is opened, and the nozzle of the male syringe is fittable in a liquid-tight manner to an inner side of the packing.

8. The syringe kit according to claim 7, wherein:
the cylindrical portion comprises:
   a first cylindrical portion provided with the projection and having an outer diameter smaller than an inner diameter of the screw, and
   a second cylindrical portion formed adjacent to a proximal end side of the first cylindrical portion and having an outer diameter larger than the outer diameter of the first cylindrical portion; and
the screw is on a distal end portion of the lock adapter and fits to the second cylindrical portion in a state in which the fitting of the nozzle to the cylindrical portion via the packing is completed.

9. The syringe kit according to claim 7, wherein:
in a state in which the fitting of the nozzle to the cylindrical portion via the packing is completed, the packing is held between the cylindrical portion and the nozzle in a compressed state over an entire circumference of the packing.

10. The syringe kit according to claim 7, wherein:
the cylindrical portion comprises an abutment portion that restricts a fitting depth of the nozzle into the cylindrical portion by abutment of a distal end of the lock adapter when the nozzle is fitted to the cylindrical portion via the packing.

11. A female syringe comprising:
a female syringe barrel comprising:
   a hollow barrel body having an inner peripheral surface on which a gasket is slidable,
   a cylindrical portion extended in a distal end direction from a distal end of the barrel body, into which a nozzle of a male syringe is insertable, and
   a projection with which a screw of a lock adapter of the male syringe is screwable;
a hollow cylindrical packing made of an elastic material and arranged in the cylindrical portion; and
a cap detachably attached to the cylindrical portion and configured to close, in a liquid-tight manner, an opening of the packing, wherein the cap comprises a base and a convex fitting portion projecting in a proximal end direction from the base;
wherein the female syringe is configured such that, when the cap is detached from the cylindrical portion, the packing remains in the cylindrical portion, the opening is opened, and the nozzle of the male syringe is fittable in a liquid-tight manner to an inner side of the packing;
wherein at least in a state in which the cap is attached to the cylindrical portion and in a state in which the nozzle of the male syringe is fitted in a liquid-tight manner to the inner side of the packing, an outer peripheral surface of the packing is in close contact with an inner peripheral surface of the cylindrical portion so as to make a full circle of a liquid tight sealing portion in a circumferential direction of the cylindrical portion; and
wherein the packing is held between the inner peripheral surface of the cylindrical portion and an outer peripheral surface of the convex fitting portion in a compressed state over an entire circumference of the packing.

12. The female syringe according to claim 11, wherein:
an inner peripheral surface of the packing comprises:
   a first fitting surface to which the convex fitting portion is fitted, and
   a second fitting surface to which the nozzle of the male syringe is fittable, wherein the second fitting surface is formed on a proximal end side of the first fitting surface, and wherein an inner diameter of the second fitting surface is smaller than an inner diameter of the first fitting surface.

13. A female syringe comprising:
a female syringe barrel comprising:
   a hollow barrel body having an inner peripheral surface on which a gasket is slidable,
   a cylindrical portion extended in a distal end direction from a distal end of the barrel body, into which a nozzle of a male syringe is insertable, and
   a projection with which a screw of a lock adapter of the male syringe is screwable;
a hollow cylindrical packing made of an elastic material and arranged in the cylindrical portion; and a cap detachably attached to the cylindrical portion and configured to close, in a liquid-tight manner, an opening of the packing;

wherein the female syringe is configured such that, when the cap is detached from the cylindrical portion, the packing remains in the cylindrical portion, the opening is opened, and the nozzle of the male syringe is fittable in a liquid-tight manner to an inner side of the packing;

wherein at least in a state in which the cap is attached to the cylindrical portion and in a state in which the nozzle of the male syringe is fitted in a liquid-tight manner to the inner side of the packing, an outer peripheral surface of the packing is in close contact with an inner peripheral surface of the cylindrical portion so as to make a full circle of a liquid tight sealing portion in a circumferential direction of the cylindrical portion;

wherein a radially projecting engaging convex portion is provided on one of the inner peripheral surface of the cylindrical portion and the outer peripheral surface of the packing;

wherein an engaging concave portion having a depth in a radial direction is provided on the other of the inner peripheral surface of the cylindrical portion and the outer peripheral surface of the packing; and wherein movement of the packing in an axial direction with respect to the cylindrical portion is restricted by engagement between the engaging convex portion and the engaging concave portion.

14. The female syringe according to claim 13, wherein:
the engaging concave portion is provided on the outer peripheral surface of the packing.

\* \* \* \* \*